United States Patent [19]

Sasaki et al.

[11] Patent Number: 5,662,780
[45] Date of Patent: Sep. 2, 1997

[54] PROCESS FOR PURIFYING ACETIC ACID

[75] Inventors: Takaharu Sasaki; Masayuki Fujimoto; Takashige Miyanari; Hiroshi Nishino, all of Oita, Japan

[73] Assignee: Showa Denko K.K., Tokyo, Japan

[21] Appl. No.: 613,204

[22] Filed: Mar. 6, 1996

[30] Foreign Application Priority Data

Sep. 29, 1995 [JP] Japan .................................... 7-254004

[51] Int. Cl.$^6$ ........................................................ B01D 3/36
[52] U.S. Cl. .............................. 203/81; 203/83; 203/85; 562/607; 562/608
[58] Field of Search ........................... 203/81, 83, 85, 203/76, 79, 95, 96; 562/607, 608

[56] References Cited

U.S. PATENT DOCUMENTS

| | | | |
|---|---|---|---|
| 998,234 | 7/1911 | Crossley et al. | 203/83 |
| 1,698,798 | 1/1929 | Legendre | 203/83 |
| 2,384,374 | 9/1945 | Harrison | 203/81 |
| 2,438,300 | 3/1948 | Schniepp | 203/81 |
| 2,651,605 | 9/1953 | Hartley et al. | 203/85 |
| 2,698,285 | 12/1954 | Burton | 203/83 |
| 2,878,283 | 3/1959 | Othmer | 203/85 |
| 2,893,923 | 7/1959 | Luke, Jr. et al. | 203/83 |
| 3,052,610 | 9/1962 | Akaboshi et al. | 203/83 |
| 3,347,756 | 10/1967 | Snell | 203/81 |
| 3,404,175 | 10/1968 | Mercier | 203/81 |
| 3,772,156 | 11/1973 | Johnson et al. | 203/81 |
| 3,791,935 | 2/1974 | Eubanks et al. | 203/81 |
| 4,143,066 | 3/1979 | Kalcevic | 203/81 |

*Primary Examiner*—Cynthia L. Nessler
*Attorney, Agent, or Firm*—Sughrue, Mion, Zinn, Macpeak & Seas

[57] ABSTRACT

A process for purifying acetic acid which comprises: introducing a feedstock aqueous solution of acetic acid having an acetic acid concentration of from 10 to 50% by weight into an extractor; supplying an extracting medium containing isopropyl acetate in an amount from 0.6 to 3.0 times by weight the amount of the feedstock solution thereinto in such a manner that the extracting medium is made in contact with the feedstock solution; extracting acetic acid into the extracting medium; separating the extracting medium containing acetic acid from an extraction residue; supplying the extraction medium containing acetic acid into an azeotropic distillation column; distilling off the isopropyl acetate contained in the extraction medium from a top of the azeotropic distillation column via azeotropic distillation with water; condensing a distillate from the top of the azeotropic distillation column, to divide the distillate into a water-poor phase being rich in isopropyl acetate and a water-rich phase being rich in water; returning at least a portion of the water-poor phase into the extractor as the extracting medium; and recovering the acetic acid, which has been thus dehydrated and purified, from a bottom of the azeotropic distillation column.

6 Claims, 2 Drawing Sheets

PROCESS FOR PURIFYING ACETIC ACID

FIELD OF THE INVENTION

The present invention relates to a process for purifying acetic acid whereby purified acetic acid is recovered from a feedstock solution at a high efficiency with less energy consumption.

BACKGROUND OF THE INVENTION

The conventionally known methods for producing acetic acid on an industrial scale include the fermentation method; the method of carbonylation of methanol by a reaction in a homogeneous liquid phase system with the use of rhodium and iodine as a catalyst, the method of oxidation of a hydrocarbon (butane, naphtha, etc.) by a reaction in a heterogeneous solid phase system with the use of an organic-soluble salt catalyst (manganese naphthenate, cobalt naphthenate, nickel naphthenate, etc.); the ethylene two-step oxidation method which comprises oxidizing ethylene to thereby once form acetaldehyde and then oxidizing the resulting acetaldehyde in a homogeneous liquid phase system with the use of manganese acetate or a mixture of manganese acetate, copper acetate and cobalt acetate to thereby give acetic acid; and a method which comprises reacting ethylene with oxygen in a gas phase with the use of metallic palladium and heteropolyphosphoric acid as the main catalyst (JP-A-7-89896; the term "JP-A" as used herein means an "unexamined published Japanese patent application").

In each of these methods, acetic acid is obtained in the form of an aqueous solution. To obtain dehydrated and purified acetic acid, it is therefore needed to remove water from this aqueous solution by a method as inexpensive as possible.

Distillation is generally employed in order to industrially obtain purified acetic acid from an aqueous solution of acetic acid. To separate water from acetic acid by a conventional distillation method, however, it is needed to use a distillation column provided with a large number of plates (i.e., 70 or more) since the boiling point of acetic acid (117.8° C. under atmospheric pressure) is close to that of water. In addition, a large amount of water having a large heat of vaporization should be distilled off from the column top, which requires a large-scaled equipment and much energy. Due to the low relative volatility of water to acetic acid, furthermore, it is needed to set a large reflux rate at the column top, which lowers the efficiency of the process.

Various proposals have been made to solve this problem. For example, there has been known a method which comprises subjecting an aqueous solution of acetic acid (hereinafter referred to as the "feedstock solution") to azeotropic distillation together with an azeotropic agent capable of forming an azeotrope with water and thus distilling off the minimum azeotrope of water and the azeotropic agent from the column top while recovering the acetic acid thus concentrated from the column bottom (JP-B-43-16965, JP-B-61-31091, etc.; the term "JP-B" as used herein means an "examined Japanese patent publication"). Although this method is advantageous in that the reflux rate at the column top can be lowered and thus the energy required for the distillation of water can be reduced, a large amount of water should be distilled off from the column top similar to the conventional distillation methods. Thus no sufficient effect of saving energy can be achieved thereby.

As a method other than the azeotropic distillation method, there has been known the extraction method. This method generally comprises making a water-insoluble organic solvent, which is employed as the extracting medium, in contact with the feedstock solution, thus extracting acetic acid into the extracting medium phase and then separating and purifying the acetic acid from the extracted solution by, for example, distillation. An important factor of this extraction method resides in the selection of an appropriate extracting medium which has a small partition coefficient with water and allows sufficient dissolution of acetic acid therein.

Regarding the selection of an appropriate solvent, a number of proposals have been made to employ a solvent which has a boiling point higher than that of acetic acid and allows sufficient dissolution of acetic acid therein, since a solvent with a higher boiling point generally has the smaller partition coefficient with water. In JP-A-60-25949 (the term "JP-A" as used herein means an "unexamined published Japanese patent application"), for example, acetic acid is extracted from a feedstock solution with the use of a high-boiling solvent comprising a $C_7$ aliphatic ketone as the major component and, after stripping the water contained in the extracted solution, acetic acid is separated from the high-boiling solvent by distillation. In JP-B-59-35373, extraction is performed by using a tertiary amine, which has a boiling point higher than that of acetic acid, together with an oxygen-containing organic solvent, which also has a boiling point higher than that of acetic acid, and the extracted solution is dehydrated by distillation followed by the distillation of the dehydrated mixture again to thereby give the acetic acid. In JP-B-60-16410, a specific secondary amide is employed as an extracting medium and acetic acid is separated from the extracted solution by distillation. Furthermore, U.S. Pat. No. 4,143,066 proposes to use trioctylphosphine oxide as a high-boiling solvent capable of selectively extracting acetic acid.

There have been also known methods wherein a mixture of a low-boiling solvent with a high-boiling solvent is employed as an extracting medium. In JP-B-1-38095, for example, a solvent mixture comprising ethyl acetate with diisobutyl ketone is used. Further, U.S. Pat. No. 2,175,879 discloses a method wherein extraction and azeotropic distillation are carried out at the same time. In this method, a feedstock solution is divided into two portions and one portion is extracted with a low-boiling solvent while another portion is subjected to azeotropic distillation with the use of an azeotropic agent such as butyl acetate. By the multipurpose use of the heat of condensation of the gas at the azeotropic distillation column top, the low-boiling solvent in the extracted solution is recovered from acetic acid via distillation, thus saving energy.

When a high-boiling solvent is used as an extracting medium in the extraction methods or the extraction/azeotropic distillation methods as described above, the amount of water taken up into the extracting medium phase is generally reduced but the partition coefficient thereof with acetic acid is also lowered. As a result, the extracting medium should be used in a large amount and, in its turn, the scale of the equipment is enlarged. In the subsequent step of the separation of acetic acid from the extracting medium by distillation, moreover, it is needed to distill off acetic acid having a relatively large latent heat of evaporation from the column top, which brings about an increase in the energy cost. When this separation is performed via the minimum azeotropic distillation with water, the extracting medium has a boiling point higher than that of acetic acid and thus its minimum azeotropic distillation temperature is close to the boiling point of acetic acid. Accordingly, it is difficult to obtain highly pure acetic acid at a high yield in this case.

The method, wherein a mixture comprising a low-boiling solvent together with a high-boiling solvent is used as the extracting medium, is more beneficial than the method with the use of a low-boiling solvent alone. In the former case, however, a large amount of water is taken up into the extracting medium phase, which enlarges the load in the azeotropic distillation. In this case, it is also required to separate the high-boiling solvent form acetic acid by distillation. Thus it is not always beneficial from the viewpoint of energy consumption.

The present invention has been completed in order to solve the above-mentioned problems.

SUMMARY OF THE INVENTION

An object the present invention is to provide a process for purifying acetic acid whereby purified acetic acid is efficiently recovered from a feedstock solution with less energy consumption.

Other objects and effects of the present invention will be apparent from the following description.

The present invention relates to a process for purifying acetic acid which comprises:

introducing a feedstock aqueous solution of acetic acid having an acetic acid concentration of from 10 to 50% by weight into an extractor;

supplying an extracting medium containing isopropyl acetate in an amount from 0.6 to 3.0 times by weight the amount of the feedstock solution thereinto in such a manner that the extracting medium is made in contact with the feedstock solution;

extracting acetic acid into the extracting medium;

separating the extracting medium containing acetic acid from an extraction residue;

supplying the extraction medium containing acetic acid into an azeotropic distillation column;

distilling off the isopropyl acetate contained in the extraction medium from a top of the azeotropic distillation column via azeotropic distillation with water;

condensing a distillate from the top of the azeotropic distillation column, to divide the distillate into a water-poor phase being rich in isopropyl acetate and a water-rich phase being rich in water;

returning at least a portion of the water-poor phase into the extractor as the extracting medium; and recovering the acetic acid, which has been thus dehydrated and purified, from a bottom of the azeotropic distillation column.

In a preferred embodiment of the process for purifying acetic acid according to the present invention, the extraction residue and at least a portion of the water-rich phase are supplied into a recovery/distillation column; isopropyl acetate contained in the extraction residue and the water-rich phase is subjected to azeotropic distillation with water; a distillate distilled off from a top of the recovery/distillation column is condensed to divide into a water-poor phase being rich in isopropyl acetate and a water-rich phase being rich in water; at least a portion of the water-poor phase is discharged from a system; and a waste water is discharged from a bottom of the recovery/distillation column.

In the above preferred embodiment of the present invention, it is further preferred that the water-poor phase, which has been discharged from the system, is introduced into an esterification reactor together with acetic acid; and isopropyl alcohol, which has been produced by hydrolysis of isopropyl acetate, is converted into isopropyl acetate followed by recovery.

In another preferred embodiment of the process for purifying acetic acid according to the present invention, the extraction residue is supplied into an extracting medium recovery column; and a distillate distilled off from a top of the extracting medium recovery column is returned to the extractor.

In this preferred embodiment, it is further preferred that the water-rich phase divided from the condensed distillate from the top of the azeotropic distillation column is supplied to a stripper; a distillate distilled off from a top of the stripper is returned to the azeotropic distillation column; and water is withdrawn from a bottom of the stripper.

DETAILED DESCRIPTION OF THE INVENTION

An embodiment of the present invention will be described in detail by reference to the attached figures, but the present invention is not construed as being limited thereto.

Figure 1:
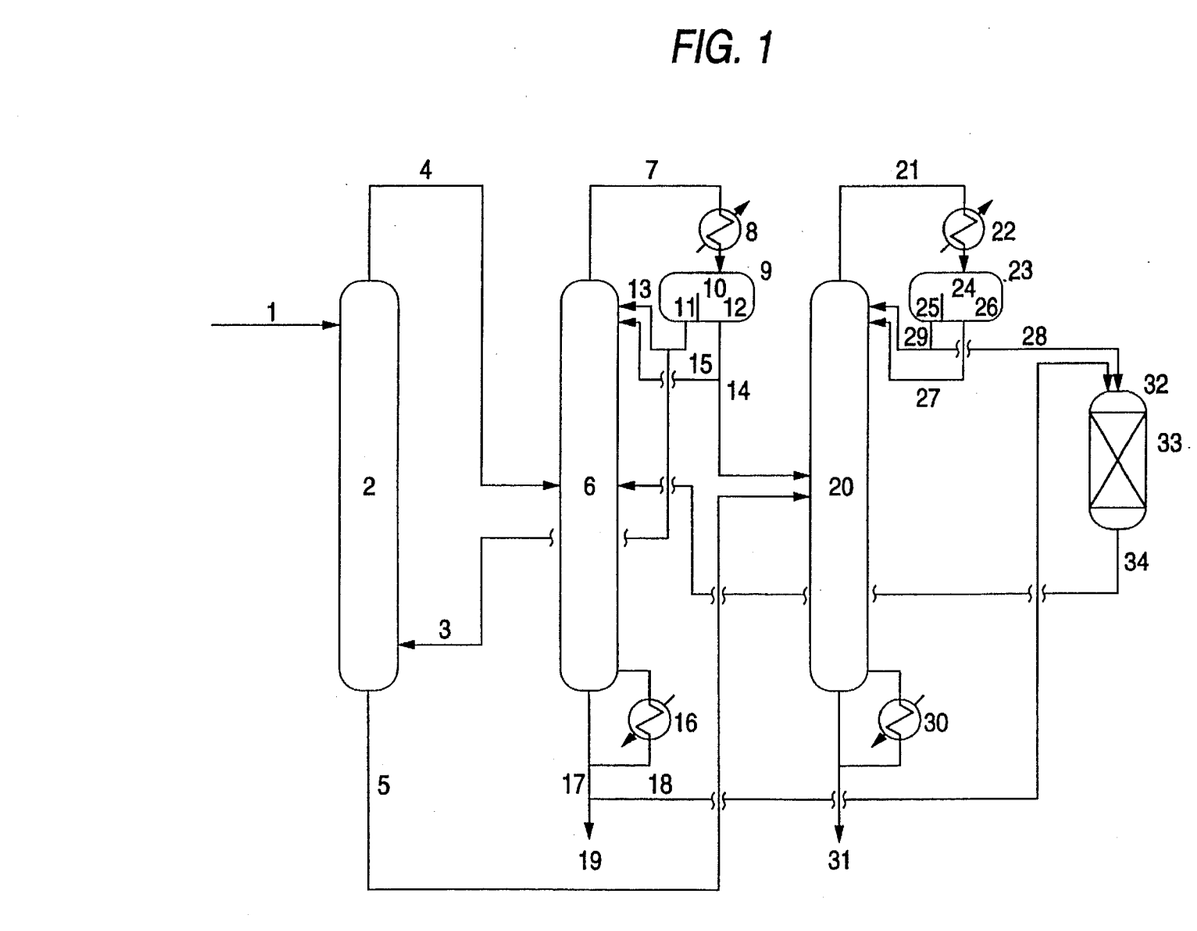
FIG. 1 is a flow diagram which shows an embodiment of the present invention.

FIG. 1 shows a flow diagram according to an embodiment of the present invention. The equipment employed in this process roughly comprises an extractor 2, an azeotropic distillation column 6, a recovery/distillation column 20 and an esterification reactor (hereinafter referred to simply as "reactor") 32. The extractor 2 is a liquid-liquid countercurrent extractor provided with plates. The azeotropic distillation column 6 and the recovery/distillation column 20 are distillation devices each equipped with a condenser 8 or 22 and a decanter 9 or 23 at the column top and a reboiler 16 or 30 at the column bottom.

In FIG. 1, a feedstock solution 1, which contains from 10 to 50% by weight of acetic acid, is first introduced into the neighborhood of the column top of the extractor 2. Into the neighborhood of the column bottom of the extractor 2 is supplied an extracting medium comprising isopropyl acetate as the main component via a line 3. The amount of this isopropyl acetate thus supplied ranges from 0.6 to 3.0 times by weight as much as the feedstock solution. It is not necessary that the extracting medium is pure isopropyl acetate but it is sufficient that it contains isopropyl acetate as the major component, such as the water-poor phase from the compartment 11 of the first decanter 9 described hereinbelow.

In the extractor 2, the feedstock solution 1 comes into contact counter currently with the extracting medium 3 both in the form of a liquid. Thus the acetic acid in the feedstock solution 1 is extracted into the extracting medium phase, and the mixture is separated into an extracted solution containing a major amounts of isopropyl acetate and acetic acid with a minor amount of water, and an extraction residue containing a major amount of water with a minor amount of isopropyl acetate. The acetic acid-containing extracted solution thus separated is supplied into the azeotropic distillation column 6 via a line 4. The extraction residue 5 is discharged from the column bottom of the extractor 2.

The extracted solution 4 from the extractor 2 contains water, which has been distributed on the extraction step, in addition to isopropyl acetate and acetic acid. When the extracted solution 4 is supplied into the azeotropic distillation column 6, the isopropyl acetate and water contained therein form a minimum azeotrope which are then distilled off as an azeotropic distillate 7 from the column top.

The azeotropic distillate 7 from the column top is condensed by the condenser 8 and then introduced as the column top condensate into the first decanter 9.

This decanter 9 has a bulkhead 10 by which the lower part of the tank is divided into two compartments 11 and 12. The column top condensate introduced into the first decanter 9 is then introduced into one compartment 12 where it is divided by liquid/liquid separation based on the difference in specific gravity into a water-rich phase, which contains water as the main component together with a minor portion of the isopropyl acetate and has a large specific gravity, and a water-poor phase, which contains isopropyl acetate as the main component together with a minor portion of water and has a relatively small specific gravity.

Then the water-rich phase is continuously withdrawn at a regulated rate from the bottom of the compartment 12 in such a manner that the water-poor phase alone flows beyond the bulkhead 10 into another compartment 11. Thus the surface levels of the water-rich phase and the water-poor phase are regulated so as to separate the water-rich phase in the compartment 12 and the water-poor phase in the compartment 11 with the bulkhead 10. In some cases, a part of the water-rich phase in the compartment 12 withdrawn from the bottom of the compartment 12 may be returned into a definite feed plate in the neighborhood of the top of the recovery/distillation column 6 via a line 15. However, at least a portion of the water-rich phase in the compartment 12 is discharged via a line 14.

A portion of the water-poor phase flowing into the compartment 11 is returned into a definite feed plate in the neighborhood of the top of the azeotropic distillation column 6 via a line 13, while the residue thereof is circulated via a line 13 into the above-mentioned extractor 2 where it is reused as the extracting medium.

Thus purified acetic acid 17, which is substantially free from water or isopropyl acetate, is obtained from the bottom of the azeotropic distillation column 6.

The extraction residue 5 discharged from the bottom of the extractor 2 and the water-rich phase 14 discharged from the compartment 12 of the decanter 9 contain isopropyl acetate distributed into water and isopropyl alcohol formed by the hydrolysis of isopropyl acetate. To efficiently recover these substances, therefore, the extraction residue 5 and the water-rich phase 14 are supplied into the feed plate of the recovery/distillation column 20.

In the recovery/distillation column 20, isopropyl acetate and isopropyl alcohol form a minimum azeotrope together with water which is then subjected to azeotropic distillation and distilled off from the column top as a recovery column top gas 21. The recovery column top gas 21 is condensed by the condenser 22 and fed as a condensate into a second decanter 23. Similar to the above-mentioned first decanter 9, the second decanter 23 has a bulkhead 24 by which the lower part of the tank is divided into two compartments 25 and 26.

The condensate fed into the second decanter 23 is then introduced into one compartment 26 where it is divided by liquid/liquid separation based on the difference in specific gravity into a water-rich phase in the compartment 26, which contains water as the main component together with a minor portion of the azeotropic agent (isopropyl acetate and isopropyl alcohol) and has a large specific gravity, and a water-poor phase in the compartment 25, which contains the azeotropic agent as the main component together with a minor portion of water and has a small specific gravity. The water-rich phase in the compartment 26 is withdrawn from the bottom of the compartment 26 via a line 27 and circulated into an appropriately selected feed plate in the neighborhood of the top of the recovery/distillation column 20. However, if the liquid/liquid separation cannot be performed due to, for example, a high concentration of isopropyl alcohol in the condensate, then the contents of the compartment 26 are not circulated into the recovery/distillation column 20 via the line 27 but treated in the same manner as the one employed in treating the contents of the compartment 25.

A portion of the water-poor phase in the compartment 25 in the decanter 23 may be, in some cases, circulated into an appropriately selected feed plate in the neighborhood of the top of the recovery/distillation column 20 via a line 29, while the residue thereof is withdrawn as a concentrate 28 and fed into the reactor 32.

By the azeotropic distillation in this recovery/distillation column 20, isopropyl acetate and isopropyl alcohol contained in the extraction residue 5 from the extractor 2 and the water-rich phase 14 discharged from the compartment 12 of the decanter 9 are concentrated and recovered into a line 28, while the waste water 31 is discharged from the column bottom.

The concentrate 28 is then introduced into the reactor 32 to react the isopropyl alcohol contained therein with acetic acid and recover the isopropyl acetate thus formed. The acetic acid for this esterification can be obtained by taking up some portion of the bottom solution 17 from the azeotropic distillation column 6 and supplying it via a line 18.

The reactor 32 also contains an acid catalyst 33 for the esterification (for example, a strongly acidic cation exchange resin or heteropolyphosphoric acid such as phosphotungstic acid).

The reaction mixture 34, which is rich in isopropyl acetate obtained by this reaction, can be circulated and reused by, for example, supplying into the azeotropic distillation column 6.

In accordance with the process for purifying acetic acid as described above by reference to FIG. 1, purified acetic acid, which is substantially free from water or isopropyl acetate, is recovered from the feedstock solution 1 containing form 10 to 50% by weight of acetic acid, as the bottom solution 19 from the azeotropic distillation column 6, while the water contained in the feedstock solution 1 is discharged as the waste water 31 from the bottom of the recovery/distillation column 20.

In this purification process shown in FIG. 1, it is not necessary to distill off a large amount of water or acetic acid from the column top. From the tops of the azeotropic distillation column 6 and the recovery/distillation column 20, minimum azeotropes each having a boiling point sufficiently lower than that of acetic acid are distilled off. Therefore, this process can be carried out at a low reflux rate with less energy consumption.

Figure 2:
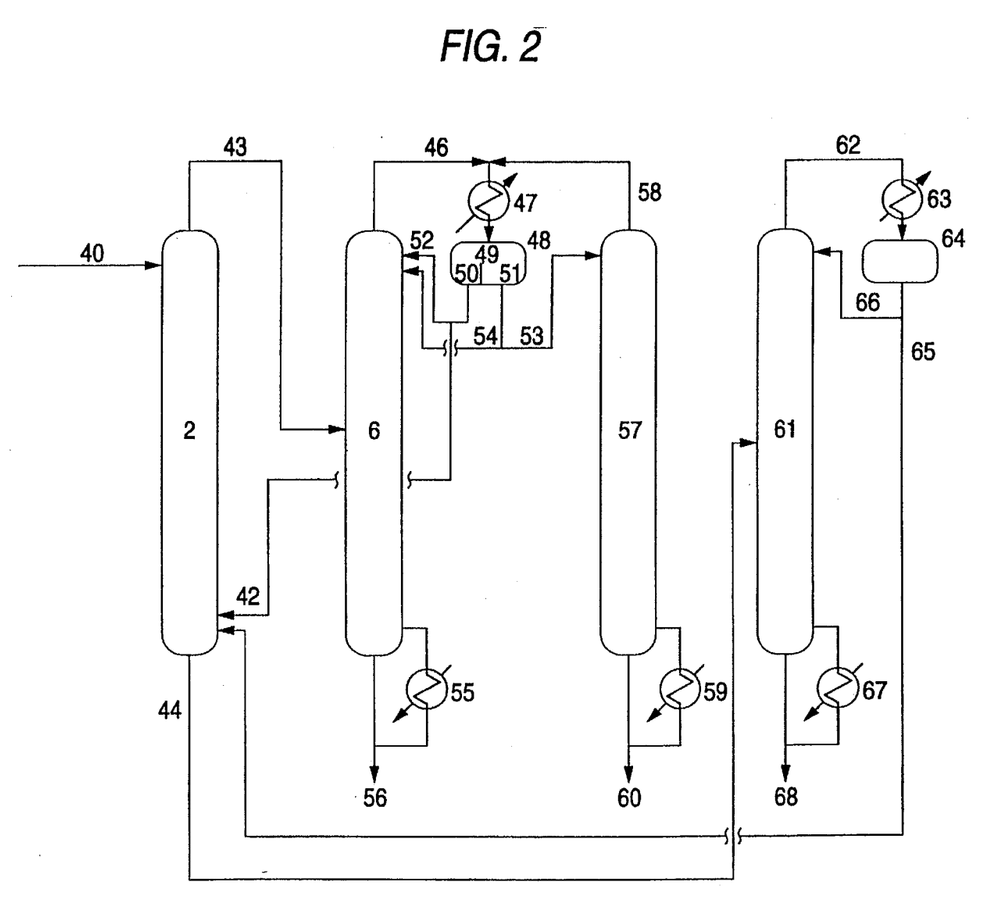
FIG. 2 is a flow diagram which shows another embodiment of the present invention.

FIG. 2 shows a flow diagram according to another embodiment of the present invention. The equipment employed in this embodiment roughly comprises an extractor 2, an azeotropic distillation column 6, a stripper 57, and an extracting medium recovery column 61. The extractor 2 and the azeotropic distillation column 6 are the same as the embodiment shown in FIG. 1. The stripper 57 is equipped with a reboiler 59 at the column bottom. The extracting medium recovery column 61 is equipped with a condenser 63 and a decanter 64 at the column top and a reboiler 67 at the column bottom.

In FIG. 2, the extraction of acetic acid by an extracting medium in the extractor 2 and the separation of purified acetic acid from the extracted solution in the azeotropic distillation column 6 are conducted in the similar manner as in the embodiment shown in FIG. 1. In FIG. 2, numeral 40 denotes a feedstock solution, 42 denotes an extracting medium, 43 denotes an extracted solution, 46 denotes an azeotropic distillate, 47 denotes a condenser, 48 denotes a first decanter, 49 denotes a bulkhead, 50 and 51 denote compartments, 52 denotes a line for returning the water-poor phase to the azeotropic distillation column 6, 54 denotes a line for returning the water-rich phase to the azeotropic distillation column 6, 55 denotes a reboiler, and 56 denotes a line for withdrawing purified acetic acid.

In FIG. 2, the extraction residue 44 discharged from the bottom of the extractor 2 is supplied into the extraction medium recovery column 61. In the extraction medium recovery column 61, the extraction residue 44 is subjected to distillation to separate water therefrom, which is then withdrawn from a line 68. A distillate 62 distilled from the extraction medium recovery column 61 containing the extracting medium is condensed by the condenser 63 and the decanter 64. The condensate in the decanter 64 is then returned to the extractor 2 through a line 65 as the extracting medium. A part of the condensate may be returned to the extraction medium recovery column 61 through a line 66.

The azeotropic distillate 46 from the top of the azeotropic distillation column 6 is condensed by the condenser 47 and separated into a water-rich phase and a water-poor phase in the decanter 48. A portion of the water-poor phase is returned into the azeotropic distillation column via line 52 and the residue thereof is circulated via a line 42 into the extractor 2 as the extracting medium in the similar manner as in the embodiment shown in FIG. 1.

A part of the water-rich phase may be returned into the azeotropic distillation column 6 in the similar manner as in the embodiment shown in FIG. 1. The residue of the water-rich phase is discharged from a line 53 and supplied into the stripper 57. The water-rich phase is subjected to distillation in the stripper 57. The distillate distilled off from the top of stripper 57 containing water and the extracting medium is supplied to the condenser 47 to return into the azeotropic distillation column 6. Water is withdrawn from the bottom of the stripper 57 via a line 60.

In the process for purifying acetic acid of the present invention, isopropyl acetate is selected as the extracting medium for the following reasons. Isopropyl acetate has a relatively small partition coefficient with water at the extraction and is highly compatible with water, thus ensuring efficient separation of acetic acid from water. Also, the boiling point of isopropyl acetate alone (88.5° C.) and the minimum azeotropic distillation temperature thereof with water (76.6° C.) are sufficiently lower than the boiling point of acetic acid (117.8° C.). Thus the energy required for the separation can be reduced and, moreover, the reflux rate at the distillation/recovery step can be regulated to a low level, which contributes to the improvement in the efficiency of the process.

As the feedstock solution 1, an aqueous solution with an acetic acid concentration ranging from 10 to 50% by weight can be used. The concentration range as defined above is the optimum one when isopropyl acetate is employed as the extracting medium. When the acetic acid concentration is lower than 10% by weight, it is required to use a large amount of isopropyl acetate as the extracting medium in order to elevate the yield of the acetic acid. In this case, much energy is consumed for the recovery of the isopropyl acetate from the azeotropic distillation column 6 and the recovery/distillation column 20. When the concentration of acetic acid in the feedstock solution exceeds 50% by weight, on the other hand, a relatively large amount of water is distributed into the extracted solution 4 in the extractor 2 compared with the amount of the water contained in the extraction residue 5. In this case, the ability to selectively separate acetic acid is substantially deteriorated.

The amount of the isopropyl acetate to be supplied into the extractor 2 is from 0.6 to 3.0 times by weight the amount of the feedstock solution 1. When the amount of the isopropyl acetate is less than 0.6 times by weight the amount of the feedstock solution, the yield of the acetic acid is lowered. When the amount of the isopropyl acetate exceeds 3.0 times by weight, on the other hand, excessive energy is required for the distillation/recovery of the isopropyi acetate in the azeotropic distillation column 6.

It is preferred that the extraction temperature in the extractor 2 is from 10° to 80° C. When the extraction temperature falls within this range, the liquid-liquid separation into the isopropyl acetate phase and the aqueous phase can be smoothly performed.

In the first decanter 9 and the second decanter 23, the liquid-liquid separation is carried out to give the water-poor phase and the water-rich phase. To smoothly perform the liquid-liquid separation, it is preferable to regulate the temperature to 0° C. to 70° C.

Because of being an ester compound, isopropyl acetate is hydrolyzed in the presence of water in the extractor 2, the azeotropic distillation column 6, etc. to thereby give isopropyl alcohol. This hydrolysis is an equilibrium reaction and the equilibrium constant thereof is 0.45 as shown by the following formula.

Reaction Formula isopropyl acetate+water⇌isopropyl alcohol+acetic acid

Equilibrium Constant $$\frac{\text{isopropyl alcohol} \times \text{acetic acid}}{\text{isopropyl acetate} \times \text{water}} = 0.45$$

When isopropyl alcohol having a large partition coefficient with water is gradually accumulated in the circulation system, the extraction in the extractor 2 and the liquid-liquid separation in the decanters are disturbed thereby. It is therefore desirable that the isopropyl alcohol thus formed is reacted with acetic acid to thereby give isopropyl acetate which is then circulated and reused.

Isopropyl alcohol per se is a low-boiling compound (boiling point: 82.3° C.) and forms a three-component minimum azeotrope together with water and isopropyl acetate (minimum azeotropic distillation temperature: 75.5° C., composed of 11.0% by weight of water, 76.0% by weight of isopropyl acetate and 13.0% by weight of isopropyl alcohol). Thus it can be easily separated from acetic acid by distillation.

In the embodiment shown in Figure, the isopropyl alcohol is converted into isopropyl acetate which is then circulated and reused. Thus the extraction residue 5 from the extractor 2 and a portion 14 of the water-rich phase in the compartment 12 separated by the first decanter 9 are subjected to azeotropic distillation in the recovery/distillation column 20. Then the condensate 28, which is obtained from the recovery/distillation column top and contains isopropyl alcohol concentrated therein, is supplied together with acetic acid 18, which is a portion of acetic acid recovered from the bottom of the azeotropic distillation column, into the reactor 32 where the isopropyl alcohol is converted into isopropyl acetate.

It is preferable that the reaction mixture 34 thus obtained, which is rich in isopropyl acetate and contains acetic acid in excess, is circulated into not the extractor 2 but the azeotropic distillation column 6.

The equipment to be used in the process for purifying acetic acid of the present invention and the mode thereof are not restricted to those employed in the above-mentioned embodiment. For example, the extractor, azeotropic distillation column and recovery/distillation column may be each of plate type, packed type, rotating cylinder type, etc. The condensers, decanters, reboilers, etc. attached thereto may be either integrated thereinto or separately provided. Neither the type of the reactor nor the constitution of the catalyst is particularly restricted, so long as the smooth progress of esterification is not inhibited thereby.

The present invention is further described in more detail by referring to the following Examples, but the present invention is not construed as being limited thereto.

In the following Examples, purified acetic acid is recovered from a feedstock solution in accordance with the above-mentioned embodiments by using the equipments shown in FIGS. 1 and 2. In the following description, the term "parts by weight" means the value expressed by referring the amount of the feedstock solution as to 100 parts by weight.

EXAMPLE 1

In this example, a mixture of acetic acid (42.0% by weight) and water (58.0% by weight) was used as the feedstock solution 1 and purified by using the equipment shown in FIG. 1.

The above-mentioned feedstock solution 1 (100 parts by weight) and the extracting medium 3 (105.5 parts by weight) comprising isopropyl acetate as the main component were introduced into the extractor 2 each at a temperature of 30° C.

As the extractor 2, a vertical vibration column of the counter current liquid-liquid extraction type (corresponding to a theoretical plate number of from 4 to 6) was used. The feedstock solution 1 was introduced from the neighborhood of the column top, while the extracting medium was introduced from the neighborhood of the column bottom.

The extracted solution 4 (168.8 parts by weight) flowing from the column top of the extractor 2 was supplied into the feed plate of the azeotropic distillation column 6 and subjected to azeotropic distillation therein. At the same time, the reaction mixture 34 (3.4 parts by weight) from the reactor 32 was also supplied to the same feed plate. As this azeotropic distillation column 6, a distillation device of the Oldershaw type composed of a concentration unit having 30 plates and a recovery unit having 30 plates was used.

The column top gas 7 from the azeotropic distillation column 6 was cooled to 30° C. by the condenser 8. Then the condensate thus obtained was divided into the water-poor phase in the compartment 11 and the water-rich phase in the compartment 12 by the liquid-liquid separation in the decanter 9. A portion (172.0 parts by weight) of the water-poor phase was then returned into the neighborhood of the top of the azeotropic distillation column 6 via the line 13, while the residue (105.0 parts by weight) thereof was circulated into the extractor 2 and employed as the extracting medium 3.

The water-rich phase in the compartment 12 of the decanter 9 was not returned into the azeotropic distillation column 6 but all supplied into the recovery/distillation column 20 via the line 14.

Together with the above-mentioned water-rich phase in the compartment 12, the extraction residue 5 (36.2 parts by weight) from the extractor 2 was supplied into the recovery/distillation column 20 wherein the extracting medium was recovered by distillation. As the recovery/distillation column 20, a distillation device of the Oldershaw type composed of a concentration unit having 25 plates and a recovery unit having 25 plates was used.

When the column top gas 21 was cooled with the condenser 22, the obtained condensate could not undergo liquid-liquid separation. Thus a portion (4.0 parts by weight) thereof was returned as such into the neighborhood of the top of the recovery/distillation column 20 via the line 29, while the residual column top solution (2.5 parts by weight) was supplied as a concentrate 28 into the reactor 32.

The concentrate 28 comprised 11.1% by weight of water, 67.9% by weight of isopropyl acetate and 21.1% by weight of isopropyl alcohol.

Into the reactor 32 was supplied a portion (0.9 parts by weight) of the purified acetic acid 17 obtained from the bottom of the azeotropic distillation column 6 via the line 18, together with the concentrate 28.

The reactor 32 was packed with a cationic ion exchange resin (PK-212H, manufactured by Mitsubishi Chemical Company) as an acid catalyst 33.

The reaction mixture 34 (3.4 parts by weight), which was obtained by the esterification in the reactor 32, contained 8.3% by weight of water, 25.6% by weight of acetic acid, 50.9% by weight of isopropyl acetate and 15.3% by weight of isopropyl alcohol. In the reactor 32, isopropyl alcohol was converted into the isopropyl acetate at a conversion of 2.3%.

The reaction mixture 34 thus obtained was all supplied into the feed plate of the azeotropic distillation column 6.

By the above-mentioned operation, purified acetic acid 19 (41.0 parts by weight), which was substantially free from water, isopropyl acetate, or isopropyl alcohol, was obtained from the bottom of the azeotropic distillation column 6, while the waste water 31 was discharged from the bottom of the recovery/distillation column 20.

Table 1 shows the composition (% by weight) of the contents of each line shown in FIG. 1 and the load (parts by weight per 100 parts by weight of the feedstock solution 1) of each line.

TABLE 1

| Line | 1 | 3 | 4 | 5 | 13 | 14 | 15 | 17 | 18 | 19 | 27 | 28 | 29 | 31 | 34 |
|---|---|---|---|---|---|---|---|---|---|---|---|---|---|---|---|
| Composition (% by weight) | | | | | | | | | | | | | | | |
| Water | 58.0 | 2.9 | 16.2 | 93.4 | 2.9 | 96.6 | 0.0 | 0.0 | 0.0 | 0.0 | 0.0 | 11.1 | 11.1 | 98.2 | 8.3 |
| Acetic acid | 42.0 | 0.0 | 24.3 | 2.9 | 0.0 | 0.0 | 0.0 | 100.0 | 100.0 | 100.0 | 0.0 | 0.0 | 0.0 | 1.8 | 25.6 |
| Isopropyl acetate | 0.0 | 95.8 | 59.0 | 2.8 | 95.8 | 2.7 | 0.0 | 0.0 | 0.0 | 0.0 | 0.0 | 67.9 | 67.9 | 0.0 | 50.9 |
| Isopropyl alcohol | 0.0 | 1.3 | 0.6 | 0.9 | 1.3 | 0.7 | 0.0 | 0.0 | 0.0 | 0.0 | 0.0 | 21.1 | 21.1 | 0.0 | 15.3 |
| Load (part by weight) | 100.0 | 105.0 | 168.8 | 36.2 | 172.0 | 25.3 | 0.0 | 41.8 | 0.9 | 41.0 | 0.0 | 2.5 | 4.0 | 59.1 | 3.4 | compartment 12 by the liquid-liquid separation in the decanter 9. A portion (172.0 parts by weight) of the water-poor phase was then returned into the neighborhood of the These results show that, in accordance with the method of Example 1, purified acetic acid having a high purity could be efficiently separated from water and thus recovered from the feedstock solution 1, which contained 42.0% by weight of acetic acid, without taking out the acetic acid as a column top distillate from a distillation column. It is also shown that the extracting medium could be circulated and reused without any waste.

EXAMPLE 2

Acetic acid was purified by using the same equipment and the same method as those employed in Example 1 but varying the composition of the feedstock solution 1.

The feedstock solution 1 employed in Example 2 comprised 21.0% by weight of acetic acid and 79.0% by weight of water.

The above-mentioned feedstock solution 1 (100 parts by weight) was introduced into the extractor 2 from the neighborhood of the column top thereof, while an extracting medium (148.0 parts by weight) consisting of 2.8% by weight of water, 96.4% by weight of isopropyl acetate and 0.8% by weight of isopropyl alcohol was introduced thereinto from the neighborhood of the column bottom, each at a temperature of 30° C., followed by extraction.

The extracted solution 4 (174.1 parts by weight) flowing from the column top of the extractor 2 was supplied into the feed plate of the azeotropic distillation column 6 and subjected to azeotropic distillation therein. At the same time, the reaction mixture 34 (4.2 parts by weight) from the reactor 32 was also supplied to the same feed plate.

The column top gas 7 from the azeotropic distillation column 6 was cooled to 30° C. and the condensate thus obtained was divided into the water-poor phase in the compartment 11 and the water-rich phase in the compartment 12 by liquid-liquid separation in the first decanter 9. A portion (44.0 parts by weight) of the water-poor phase was returned into the azeotropic distillation column 6 via the line 13, while the residue (148.0 parts by weight) thereof was circulated into the extractor 2 as the extracting medium 3. The water-rich phase in the compartment 12 was not returned into the azeotropic distillation column 6 but all (8.6 parts by weight) supplied into the recovery/distillation column 20 via the line 14.

Into the recovery/distillation column 20 was supplied the extraction residue 5 (73.9 parts by weight) from the extractor 2 together with the above-mentioned water-rich phase from the line 14 to thereby distill and recover the extracting medium.

The column top gas 21 from the recovery/distillation column 20 was cooled and the condensate thus obtained was subjected to liquid-liquid separation. The water-rich phase in the compartment 26 thus obtained was all (0.3 parts by weight) returned to the recovery/distillation column 20 as the reflux 27. On the other hand, a portion (4.3 parts by weight) of the water-poor phase was returned into the recovery/distillation column 20 via the line 29 while the residue (2.9 parts by weight) thereof was supplied into the reactor 32 as the concentrate 28.

The concentrate 28 consisted of 8.6% by weight of water, 76.4% by weight of isopropyl acetate and 15.0% by weight of isopropyl alcohol.

Into the reactor 32 was supplied a portion (1.3 parts by weight) of the purified acetic acid 17 obtained from the bottom of the azeotropic distillation column 6 via the line 18 together with the concentrate 28.

The reaction mixture 34 (4.2 parts by weight) obtained by the esterification in the reactor 32 contained 6.1% by weight of water, 30.6% by weight of acetic acid, 53.5% by weight of isopropyl acetate and 9.9% by weight of isopropyl alcohol. In the reactor 32, isopropyl alcohol was converted into isopropyl acetate at a conversion of 4.2%.

The reaction mixture 34 thus obtained was all supplied into the feed plate of the azeotropic distillation column 6.

By the above-mentioned operation, purified acetic acid 19 (20.4 parts by weight), which was substantially free from water, isopropyl acetate, or isopropyl alcohol, was obtained from the bottom of the azeotropic distillation column 6, while the waste water 31 was discharged from the bottom of the recovery/distillation column 20.

Table 2 shows the composition (% by weight) of the contents of each line shown in FIG. 1 and the load (parts by weight per 100 parts by weight of the feedstock solution 1) of each line.

TABLE 2

| Line | 1 | 3 | 4 | 5 | 13 | 14 | 15 | 17 | 18 | 19 | 27 | 28 | 29 | 31 | 34 |
| --- | --- | --- | --- | --- | --- | --- | --- | --- | --- | --- | --- | --- | --- | --- | --- |
| Composition (% by weight) | | | | | | | | | | | | | | | |
| Water | 79.0 | 2.8 | 7.0 | 96.0 | 2.8 | 97.0 | 97.0 | 0.0 | 0.0 | 0.0 | 88.3 | 8.6 | 8.6 | 99.3 | 6.1 |
| Acetic acid | 21.0 | 0.0 | 11.7 | 0.8 | 0.0 | 0.0 | 0.0 | 100.0 | 100.0 | 100.0 | 0.0 | 0.0 | 0.0 | 0.7 | 30.6 |
| Isopropyl acetate | 0.0 | 96.4 | 80.8 | 2.7 | 96.4 | 2.5 | 2.5 | 0.0 | 0.0 | 0.0 | 2.8 | 76.4 | 76.4 | 0.0 | 53.5 |
| Isopropyl alcohol | 0.0 | 0.8 | 0.5 | 0.5 | 0.8 | 0.5 | 0.5 | 0.0 | 0.0 | 0.0 | 8.9 | 15.0 | 15.0 | 0.0 | 9.9 |
| Load (part by weight) | 100.0 | 148.0 | 174.1 | 73.9 | 44.0 | 8.6 | 8.6 | 21.7 | 1.3 | 20.4 | 0.3 | 2.9 | 4.3 | 79.6 | 4.2 |

These results show that, in Example 2 wherein the feedstock solution contained 21.0% by weight of acetic acid, acetic acid could be efficiently separated from water to thereby give purified acetic acid having a high purity.

EXAMPLE 3

In this example, a mixture of acetic acid (35.0% by weight) and water (65.0% by weight) was used as the feedstock solution 40 and purified by using the equipment shown in FIG. 2.

The above-mentioned feedstock solution 40 (100 parts by weight) and the extracting medium 42 (104.0 parts by weight) and 65 (5.4 parts by weight) each comprising isopropyl acetate as the main component were introduced into the extractor 2 each at a temperature of 30° C.

As the extractor 2, a vertical vibration column of the counter current liquid-liquid extraction type (corresponding to a theoretical plate number of from 4 to 6) was used. The feedstock solution 40 was introduced from the neighborhood of the column top, while the extracting medium was introduced from the neighborhood of the column bottom.

The extracted solution 43 (157.6 parts by weight) flowing from the column top of the extractor 2 was supplied into the feed plate of the azeotropic distillation column 6 and subjected to azeotropic distillation therein. As this azeotropic distillation column 6, a distillation device of the Oldershaw type composed of a concentration unit having 30 plates and a recovery unit having 30 plates was used.

The column top gas 46 from the azeotropic distillation column 6 was cooled to 30° C. by the condenser 47. Then the condensate thus obtained was divided into the water-poor phase in the compartment 50 and the water-rich phase in the compartment 51 by the liquid-liquid separation in the decanter 48. A portion (108.0 parts by weight) of the water-poor phase was then returned into the neighborhood of the top of the azeotropic distillation column 6 via the line 52, while the residue (104.0 parts by weight) thereof was circulated into the extractor 2 and employed as the extracting medium 42.

The water-rich phase in the compartment 51 of the decanter 48 was not returned into the azeotropic distillation column 6 but all supplied into the stripper 57 via the line 53. As the stripper 57, a distillation device of the Oldershaw type having 20 plates was used.

The column top gas 58 from the top of stripper 57 was returned to the condenser 47. The waste water 60 was withdrawn from the bottom of the stripper 57.

The extraction residue 44 (51.8 parts by weight) was supplied into the extracting medium recovery column 61 wherein the extracting medium was recovered by distillation. As the extracting medium recovery column 61, a distillation device of the Oldershaw type composed of a concentration unit having 25 plates and a recovery unit having 25 plates was used.

The column top gas 62 from the top of the extraction medium recovery column 61 was cooled with the condenser 63 and the condensate thus obtained was introduced into the decanter 64. A portion (16.3 parts by weight) of the condensate was returned into the neighborhood of the top of the extracting medium recovery column 61 via the line 66, while the residue (5.4 parts by weight) thereof was circulated into the extractor 2 and employed as the extracting medium via the line 65.

By the above-mentioned operation, purified acetic acid 56 (34.5 parts by weight), which was substantially free from water, isopropyl acetate, or isopropyl alcohol, was obtained from the bottom of the azeotropic distillation column 6, while the waste water 60 and 68 was discharged from the bottom of the stripper 57 and the bottom of the extracting medium recovery column 61.

Table 3 shows the composition (% by weight) of the contents of each line shown in FIG. 2 and the load (parts by weight per 100 parts by weight of the feedstock solution 40) of each line.

acetic acid, without taking out the acetic acid as a column top distillate from a distillation column. It is also shown that the extracting medium could be circulated and reused without any waste.

The process for purifying acetic acid of the present invention comprises extracting a feedstock solution, which contains from 10 to 50% by weight of acetic acid, with an extracting medium, which contains isopropyl acetate in an amount of from 0.6 to 3.0 times by weight the amount of the feedstock solution; subjecting the extracted solution thus obtained to azeotropic distillation; returning at least a portion of the water-poor phase, which has been separated from the column top distillate, into the above-mentioned extractor as the extracting medium; and recovering the dehydrated and purified acetic acid from the bottom of the azeotropic distillation column. In accordance with this process, therefore, the extraction medium can be effectively circulated and reused and thus purified acetic acid can be obtained at a high efficiency with less energy consumption.

The extraction residue from the extractor is combined with the water-rich phase from the azeotropic distillation column and supplied into the recovery/distillation column where the extracting medium component contained in the mixture is distilled by azeotropic distillation. Thus the extracting medium can be concentrated and separated from the water with less energy consumption, which makes it possible to reduce the extracting medium loss.

Moreover, the extracting medium concentrate obtained from the recovery/distillation column is esterified by adding acetic acid. Thus the isopropyl alcohol, which has been formed by the hydrolysis of the isopropyl acetate during the process, can be converted into isopropyl acetate and recovered. As a result, the loss of the isopropyl acetate can be further reduced and, at the same time, the isopropyl alcohol concentration in the extracting medium can be continuously regulated to a low level, which makes it possible to maintain a high acetic acid extraction efficiency in the extractor.

While the invention has been described in detail and with reference to specific examples thereof, it will be apparent to one skilled in the art that various changes and modifications can be made therein without departing from the spirit and scope thereof.

What is claimed is:

1. A process for purifying acetic acid which comprises:

introducing a feedstock aqueous solution of acetic acid having an acetic acid concentration of from 10 to 50% by weight into an extractor;

supplying an extracting medium containing isopropyl acetate in an amount from 0.6 to 3.0 times by weight

TABLE 3

| Line | 40 | 42 | 43 | 44 | 46 | 52 | 53 | 54 | 56 | 58 | 60 | 62 | 65 | 66 | 68 |
|---|---|---|---|---|---|---|---|---|---|---|---|---|---|---|---|
| Composition (% by weight) | | | | | | | | | | | | | | | |
| Water | 65.0 | 2.7 | 13.9 | 89.9 | 10.7 | 2.7 | 95.0 | 0.0 | 0.0 | 14.9 | 100.0 | 11.6 | 11.6 | 11.6 | 99.0 |
| Acetic acid | 35.0 | 0.0 | 21.9 | 0.9 | 0.0 | 0.0 | 0.0 | 0.0 | 100.0 | 0.0 | 0.0 | 0.0 | 0.0 | 0.0 | 1.0 |
| Isopropyl acetate | 0.0 | 94.3 | 62.2 | 3.1 | 86.5 | 94.3 | 2.5 | 0.0 | 0.0 | 42.5 | 0.0 | 29.4 | 29.4 | 29.4 | 0.0 |
| Isopropyl alcohol | 0.0 | 3.0 | 2.0 | 6.2 | 2.7 | 3.0 | 2.5 | 0.0 | 0.0 | 42.5 | 0.0 | 59.0 | 59.0 | 59.0 | 0.0 |
| Load (part by weight) | 100.0 | 104.0 | 157.6 | 51.8 | 231.1 | 108.0 | 20.3 | 0.0 | 34.5 | 1.2 | 19.1 | 21.7 | 5.4 | 16.3 | 46.4 |

These results show that, in accordance with the method of Example 3, purified acetic acid having a high purity could be efficiently separated from water and thus recovered from the feedstock solution 40, which contained 35.0% by weight of the amount of said feedstock solution thereinto in such a manner that said extracting medium contacts said feedstock solution;

extracting acetic acid into said extracting medium;

separating said extracting medium containing acetic acid from an extraction residue;

supplying said extraction medium containing acetic acid into an azeotropic distillation column;

distilling off said isopropyl acetate contained in said extraction medium from a top of said azeotropic distillation column via azeotropic distillation with water;

condensing a distillate from said top of said azeotropic distillation column, to divide said distillate into a water-poor phase being rich in isopropyl acetate and a water-rich phase being rich in water;

returning at least a portion of said water-poor phase into said extractor as said extracting medium; and recovering said acetic acid, which has been thus dehydrated and purified, from a bottom of said azeotropic distillation column.

2. A process for purifying acetic acid as claimed in claim 1, wherein said process comprises supplying said extraction residue and at least a portion of said water-rich phase into a recovery/distillation column;

azeotropically distilling isopropyl acetate contained in said extraction residue and said water-rich phase with water;

condensing a distillate distilled off from a top of said recovery/distillation column to divide into a water-poor phase being rich in isopropyl acetate and a water-rich phase being rich in water;

discharging at least a portion of said water-poor phase from a system; and discharging waste water from a bottom of said recovery/distillation column.

3. A process for purifying acetic acid as claimed in claim 2, wherein said process comprises introducing said water-poor phase, which has been discharged from the system, into an esterification reactor together with acetic acid; and converting isopropyl alcohol, which has been produced by hydrolysis of isopropyl acetate, into isopropyl acetate followed by recovery.

4. A process for purifying acetic acid as claimed in claim 3, wherein said acetic acid introduced into said esterification reactor together with said water-poor phase is a portion of acetic acid recovered from said bottom of said azeotropic distillation column.

5. A process for purifying acetic acid as claimed in claim 1, wherein the process comprises supplying said extraction residue into an extracting medium recovery column; and returning a distillate distilled off from a top of said extracting medium recovery column to said extractor.

6. A process for purifying acetic acid as claimed in claim 5, wherein the process comprises supplying said water-rich phase divided from said condensed distillate from said top of said azeotropic distillation column to a stripper;

returning a distillate distilled off from a top of said stripper to said azeotropic distillation column; and withdrawing water from a bottom of said stripper.

* * * * *